United States Patent [19]

Laghi

[11] Patent Number: 5,328,459
[45] Date of Patent: Jul. 12, 1994

[54] APPARATUS AND METHOD FOR DISPENSING AND ASPIRATING HIGH VISCOSITY MATERIALS

[76] Inventor: Aldo A. Laghi, 13 Meridian La., Ballston Lake, N.Y. 12019

[21] Appl. No.: 58,507

[22] Filed: May 6, 1993

[51] Int. Cl.⁵ .............................................. A61M 1/00
[52] U.S. Cl. ................................. 604/35; 128/DIG. 1
[58] Field of Search ...................... 604/22, 27, 30, 31, 604/33, 35, 67, 82, 83, 151, 154, 155, 902; 128/DIG. 1, DIG. 12, 655; 417/418; 222/326, 327, 389, 390, 135, 137, 145

[56] References Cited

U.S. PATENT DOCUMENTS

| | | | |
|---|---|---|---|
| 2,702,547 | 2/1955 | Glass | 128/DIG. 1 |
| 3,221,947 | 12/1965 | Penn | 222/327 |
| 3,291,151 | 12/1966 | Loken | 128/DIG. 12 |
| 3,429,313 | 2/1969 | Romanelli | 604/35 |
| 3,559,644 | 2/1971 | Stoft et al. | 604/151 |
| 3,731,679 | 5/1973 | Wilhelmson et al. | 128/DIG. 12 |
| 3,767,085 | 10/1973 | Cannon et al. | 604/82 |
| 3,955,574 | 5/1976 | Rubinstein | 604/151 |
| 4,044,757 | 8/1977 | McWhorter et al. | 604/82 |
| 4,067,479 | 1/1978 | Moline | 222/137 |
| 4,085,747 | 4/1978 | Lee | 604/154 |
| 4,232,562 | 11/1980 | Perkins | 128/DIG. 1 |
| 4,255,096 | 3/1981 | Coker, Jr. et al. | 128/DIG. 1 |
| 4,407,659 | 10/1983 | Adam | 604/155 |
| 4,563,175 | 1/1986 | LaFond | 128/DIG. 12 |
| 4,677,980 | 7/1987 | Reilly et al. | 604/228 |
| 4,846,797 | 7/1989 | Howson et al. | 128/DIG. 1 |
| 4,898,579 | 2/1990 | Groshong et al. | 604/67 |
| 5,066,283 | 11/1991 | Skrabal | 604/27 |
| 5,137,184 | 8/1992 | Jackson et al. | 222/32 |
| 5,179,983 | 1/1993 | Cordner, Jr. et al. | 128/DIG. 1 |

*Primary Examiner*—John D. Yasko
*Assistant Examiner*—Frank Wilkens
*Attorney, Agent, or Firm*—Joseph C. Mason, Jr.; Ronald E. Smith

[57] ABSTRACT

High viscosity materials are dispensed or aspirated by an assembly of cartridges having plungers reciprocally mounted within them. A device for translating rotary motion into linear motion is connected to the output shaft of a small electric motor so that operation of the motor effects linear movement of the plungers. The assembly replaces hydraulic and pneumatic systems and enables better control of the dispensing or aspirating process. In a first embodiment, a single cartridge dispenses a high viscosity material. In additional embodiments, plural cartridges are employed. In the final embodiments, the apparatus is equipped with a suitable assembly of one-way valves and other auxiliary equipment so that it can be used to perform liposuction or aspiration procedures and irrigation of surgical sites.

11 Claims, 5 Drawing Sheets

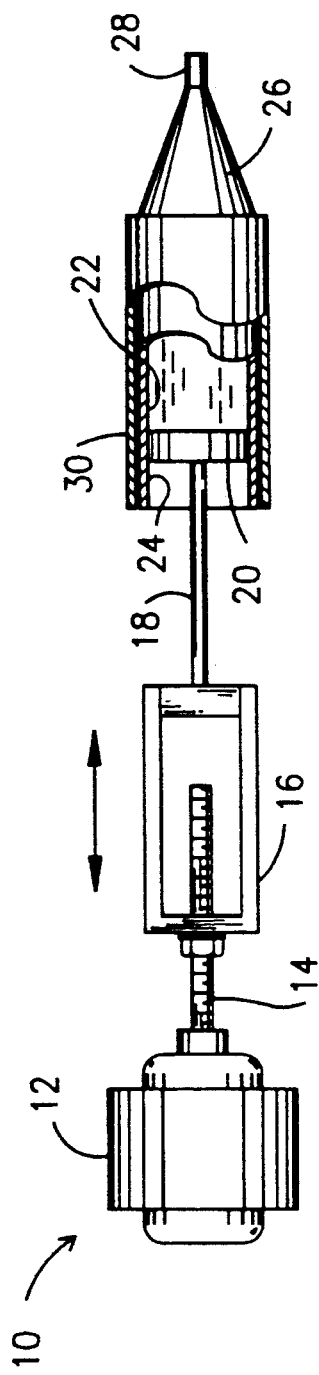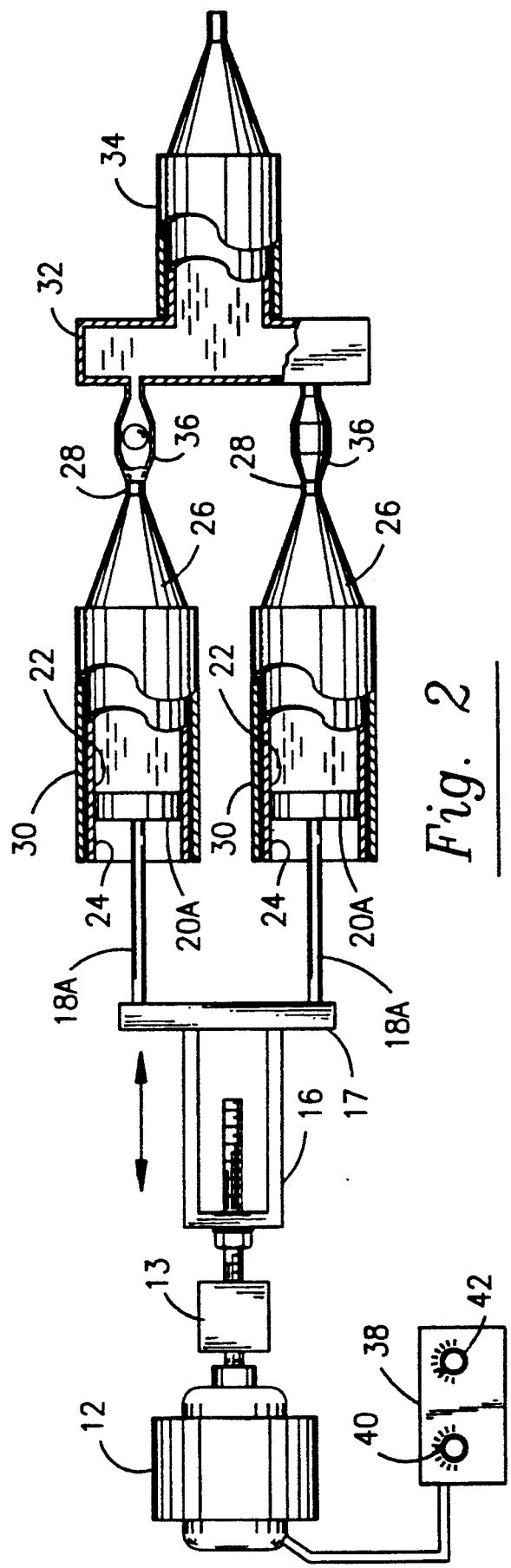

APPARATUS AND METHOD FOR DISPENSING AND ASPIRATING HIGH VISCOSITY MATERIALS

BACKGROUND OF THE INVENTION

1. Field of the Invention

This invention relates, generally, to electrically driven dispensing and aspirating machines.

2. Description of the Prior Art

Thixotropic pastes such as most silicones, polyurethanes, adhesives in general, human and animal fat, and the like, exhibit non-Newtonian, i.e., thixotropic behavior when being dispensed or aspirated. Thus, as indicated in the diagram below, very high pressures are required to produce even low flow rates of such substances.

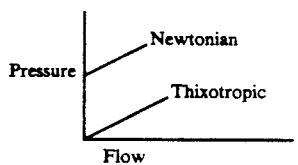

Hydraulic and pneumatic machines are currently used to dispense thixotropic materials, as well as polymers, pastes, and other high viscosity materials that exhibit non-Newtonian behavior. More particularly, such machines are used to drive pumps and pistons that dispense and meter such materials. However, there are a number of drawbacks with both of these types of machines.

For example, hydraulic machines are heavy, expensive, and somewhat insensitive in that they cannot generally be used to adequately control small volumes and low flow rates. As a result, they are usually used in large systems, i.e., those of five gallons or more.

Pneumatic machines are lighter in weight and less expensive, but due to the compressibility of air they cannot provide consistent repeatability of shot sizes and flow rates. For the same reason, they respond sluggishly to changing demands, i.e., they cannot respond instantaneously to changes in flow rates as required in many applications. Where thixotropic materials are being handled, unacceptably large air cylinders are required to produce even very small deliveries.

What is needed, then, is a revolutionary, entirely new way to dispense and aspirate materials exhibiting high viscosity. Those of ordinary skill in this art, however, are continuing to refine the existing hydraulic and pneumatic systems in the belief that their respective limitations can be overcome if enough refinements can be made.

SUMMARY OF THE INVENTION

The present invention revolutionizes the art by eschewing both hydraulic and pneumatic systems in favor of highly novel systems that employ small, electrically-driven motors.

In a first embodiment, a gearmotor or a stepper motor has an output shaft connected to a translating means for translating the rotary motion of the output shaft into linear movement, and said translating means drives a plunger into a cylinder that dispenses high viscosity material through a nozzle.

In a second embodiment, two or more cylinders and plungers are provided, and the plungers are yoked together so that linear movement of the translating means effects simultaneous and corresponding linear movement in each of the plungers with respect to its associated cylinder so that each cylinder dispenses the same amount of high viscosity material. The nozzles of each cylinder are in fluid communication with a common mixing manifold where the contents of the respective cylinders are mixed; due to the yoking, the ratio of the mixed components is fixed.

In a third embodiment, two or more cylinders and plungers are provided, and the nozzles of the cylinders are in fluid communication with a common mixing manifold, but the respective plungers are not yoked together. Moreover, the respective plungers are under independent control so that the multiple components in the multiple cylinders may be mixed in a variable ratio.

The translating means in the fourth embodiment is not connected to a plunger that is driven into a cylinder as in the first three embodiments. Instead, the translating means is connected to the plunger or piston of a conventional pump of the type designed to dispense high viscosity materials. Thus, the translating means replaces the hydraulic or pneumatic control means for said pumps, thereby enabling infinite adjustability of the ratios of materials being mixed, better speed control, constant delivery, and high torque at low power expenditure, all at lower cost.

In the last two embodiments, a pair of cylinders are disposed in axial alignment with one another, with their open ends facing one another and their nozzle ends pointing in opposite directions. A plunger rod has a plunger at its opposite ends, each of which is aligned with the open end of its associated cylinder, and the same motor and translating means of the other embodiments is employed to obtain reciprocation of the rod so that the plungers alternatively reciprocate within their respective cylinders. The nozzle of each cylinder is flanked by a pair of check valves so that one nozzle pumps while the other aspirates.

More particularly, in the fifth embodiment, the vacuuming capabilities of the system are harnessed to enable a physician to perform liposuction, and in the sixth embodiment, the pumping capabilities of the system are harnessed to perform irrigation of a surgical site.

In all of the embodiments, the cylinders may be made of a relatively inexpensive material such as plastic so that they may be disposed of after use. This enhances the utility of the devices in medical environments. Non-disposable sleeve members of metallic or other suitable strong materials slidingly receive the plastic cylinders to prevent their radial expansion during the dispensing process.

Thus it is clear that a primary object of this invention is to advance the art of handling high viscosity and very high viscosity materials by eliminating reliance upon hydraulic and pneumatic control systems.

A related object is to disclose a plurality of embodiments that employ the novel concepts of this invention, to thereby suggest still further embodiments.

More specific objects are to provide means for lowering the costs of dispensing and mixing such materials and to enhance the controllability of the mixing process.

Still another object is to provide a unique system having disposable parts so that the system may be advantageously employed in medical environments.

These and other important objects, features and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 1 is a diagrammatic representation of a first embodiment of the invention;

FIG. 2 is a diagrammatic representation of a second embodiment of the invention;

Similar reference numerals refer to similar parts throughout the several views of the drawings.

DETAILED DESCRIPTION OF THE PREFERRED EMBODIMENT

Figure 3:
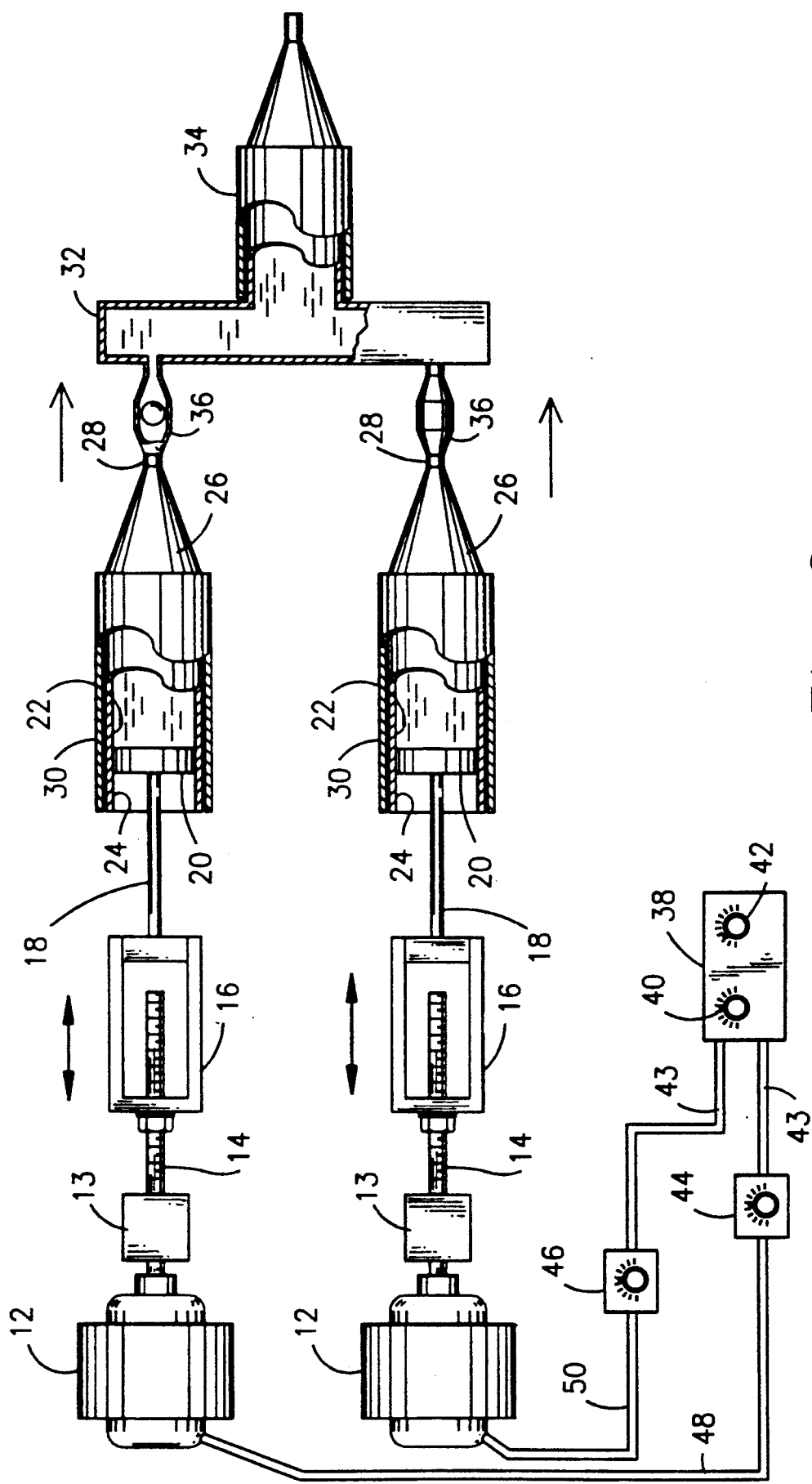
FIG. 3 is a diagrammatic representation of a third embodiment of the invention.

Referring now to FIG. 1, it will there be seen that a first illustrative embodiment of the invention is denoted 10 as a whole. Apparatus 10 includes a small motor means 12 that is preferably an electric motor of the gearmotor or stepper motor type. Rotatable output shaft 14 is connected in driving relation to a ball slide and screw assembly 16 or in the alternative to an acme thread and nut assembly; reference numeral 16 should be understood as indicating both of said assemblies. As is well-known, assembly 16 is a translating means for translating the rotary motion of an output shaft into linear motion. Assembly 16 is connected to a plunger rod 18 having plunger 20 fixedly secured to the distal free end thereof, and said plunger 20 is in axial alignment with hollow cartridge member 22. Cartridge member 22 has open proximal end 24 that slideably receives plunger 20 when the apparatus is in operation, and a tapered distal end 26. Nozzle means 28 is mounted to said distal end and is in fluid communication with the hollow interior of the cartridge so that it dispenses the material disposed within said hollow interior when said plunger travels from the proximal end thereof to the distal end thereof.

Metallic sleeve 30 ensleeves cylinder 22 and prevents its radial expansion under the very high pressures (often exceeding one thousand pounds per square inch) produced by the passage of the plunger 20 therethrough. Thus, cylinder 22 may be made of plastic or other weak, disposable material.

The arrangement of parts as depicted in FIG. 1 has utility when a single component is to be dispensed. When it is desired to mix two or more components in a fixed ratio to one another, the apparatus of FIG. 2 is employed. Translating means 16 is connected to the yoke means 17 for plunger rods 18A, 18A. Plunger rods 18A, 18A are yoked together as depicted so that they move in unison with one another; each has a plunger 20A, 20A at its distal free end. Cylinders 22, 22 are ensleeved in sleeve members 30, 30, and nozzles 28, 28 are in fluid communication with a mixing manifold 32; a static or dynamic mixer 34 is downstream of said mixing manifold, in fluid communication therewith. One-way valves 36, 36 are disposed between nozzles 28, 28 and mixing manifold 32. Motor 12 is under the control of control means 38 which includes a speed control means 40 and a total shot control 42. Although the ratio of dispensed materials is fixed due to the yoking of the plungers, the ratio need not be 1:1. More particularly, the diameters of the cylinders 22A, 22A may be different to produce fixed ratios other than 1:1.

The apparatus of FIG. 3 has utility in applications where multiple components are to be mixed with one another at variable ratios. Each motor means, translating means, plunger, cylinder, and sleeve is the same as in the first embodiment, but there are two or more sets thereof as depicted and each set is independent of the other, i.e., there is no yoking means 17 that ties the plunger rods 18 together. The mixing manifold, one-way valves, and mixer are the same as in the second embodiment, as is control means 38 that includes speed control means 40 and shot control means 42. However, ratio control means 44 and 46 are added to this embodiment; each is in electrical communication with its associated electric motor 12 over lines 48, 50, respectively. Note that each ratio control means 44, 46 is under the control of control means 38 by way of lines 43, 45. In this manner, each motor means 12 is independently controlled by speed control 40, shot control 42, and its associated ratio control means 44 or 46.

Figure 4:
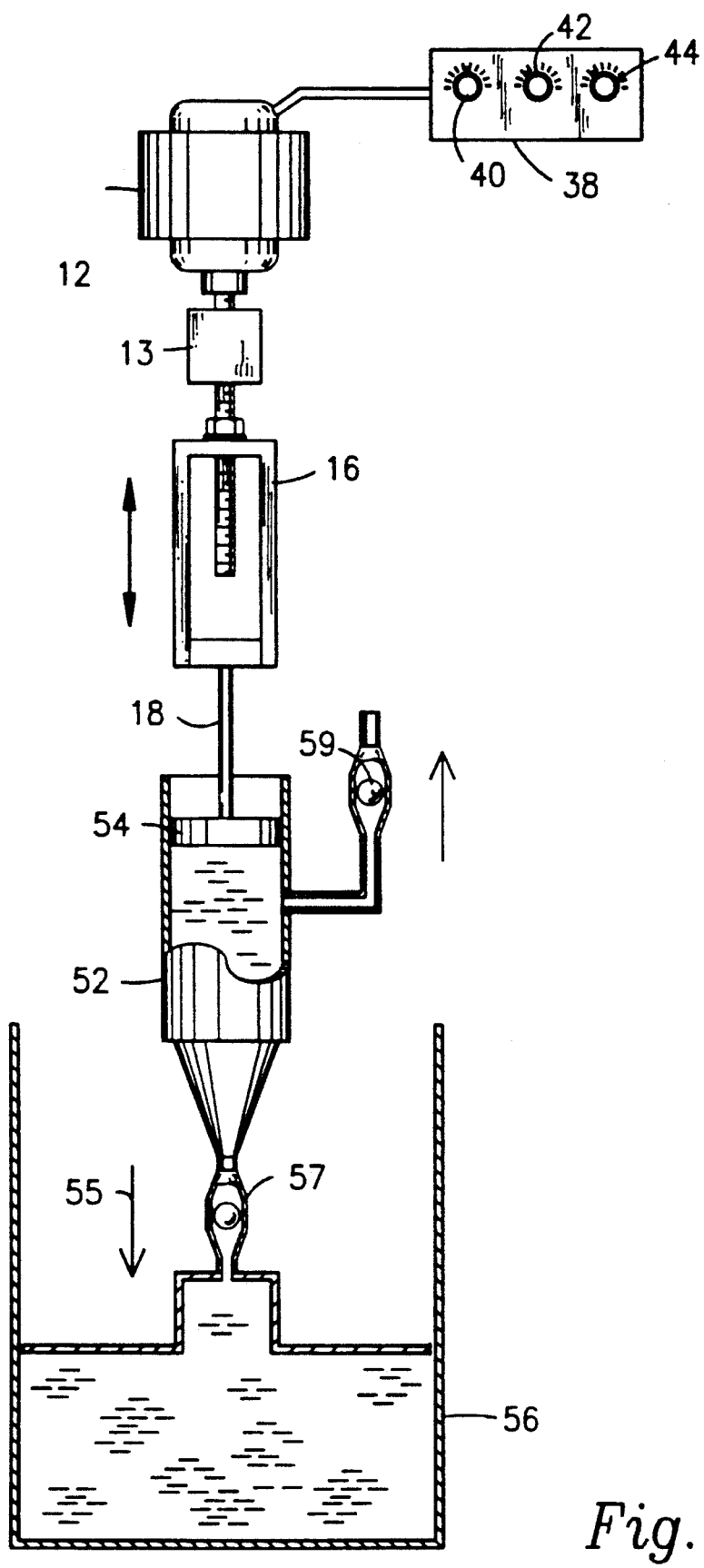
FIG. 4 is a diagrammatic representation of a fourth embodiment of the invention.

Reference numeral 52 in FIG. 4 indicates a conventional pump and its plunger is denoted 54; a conventional drum, pail, or tank is denoted 56. One-way valve 57 permits fluid flow in the direction of arrow 55, but prevents reverse flow; one-way check valve 59 does the same. Such pumps heretofore have always been hydraulically or pneumatically controlled; in this embodiment of the invention, however, the instantaneous position of plunger 54 is under the control of translating means 16 and motor means 12 which are under the control of control means 38; said control means 38 includes speed control means 40, shot control means 42, and ratio control means 44.

Figure 5:
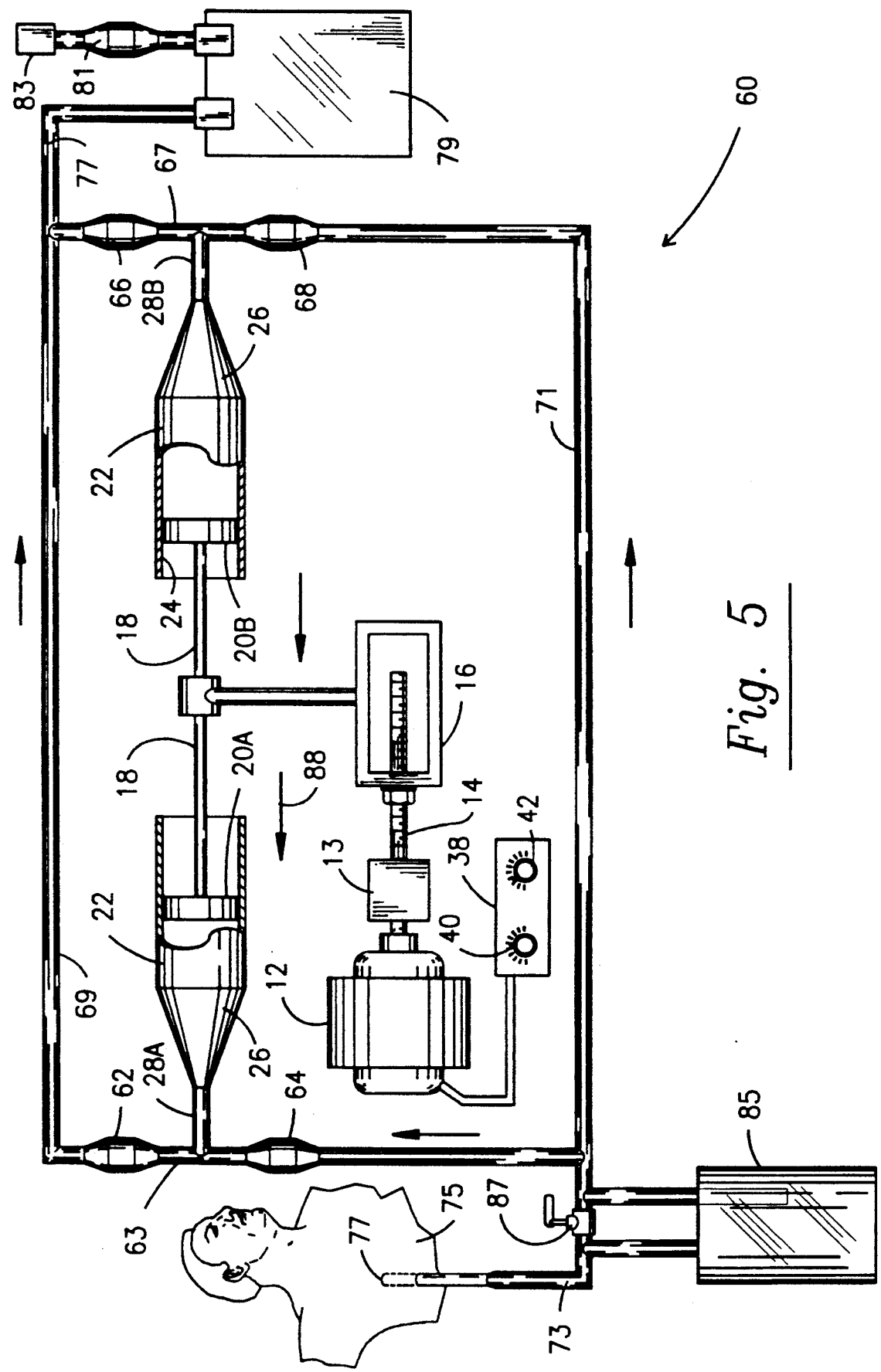
FIG. 5 is a diagrammatic representation of a fifth embodiment of the invention.

An aspiration/liposuction machine is diagrammatically depicted in FIG. 5 and is denoted 60 as a whole. A pair of cylinders 22, 22 are disposed in axial alignment with one another and their respective nozzles 28A, 28B point away from each other, i.e., their respective open proximal ends 24, 24 are in facing relation to one another. Sleeves 30 are not shown to simplify the drawing. A single plunger 18A having plungers 20A, 20B mounted on its opposite ends is mounted for reciprocation within said cylinders 22A, 22A, and the instantaneous position of said plunger 18A is under the control of translating means 16 which is in turn connected to motor means 12 as in the other embodiments. Said motor is under the control of control means 38 having speed control means 40 and total volume control means 42.

One-way valves 62, 64 are positioned in line 63 on opposite sides of nozzle 28A, and one-way valves 66, 68 are positioned in line 67 on opposite sides of nozzle 28B as shown. Lines 69 and 71 provide fluid communication between lines 63 and 67, line 73 interconnects lines 63 and 71 to the surgical site, indicated as patient 75, and line 77 interconnects lines 67 and 69 to drain bag 79.

Relief valve 81 and filter 83 may also be provided with drain bag 79. Moreover, vacuum canister 85 is connected to line 73 through valve means 87; it collects the fatty deposits that are removed from the patient during the liposuction process. Drain bag 79 collects the aerosols or smaller particles that may not be collected by vacuum canister 85. Thus, it enhances the safety of those in the operating theater because said aerosols may carry disease-causing agents.

Since plungers 20A and 20B share a common yoke 18A, one of them is aspirating at the same time the other one is expiring. For example, when plunger 20A moves in the direction indicated by directional arrow 88, cylinder 20A will expel the air therewithin and cylinder 20B will draw air into it. The air flows in the opposite direction when plunger 18A moves in the opposite direction. Due to the arrangement of the check valves 62, 64, 66, and 68 as depicted, this assembly has utility in performing liposuction or aspiration of body fluids and other fluids during any type of surgery (including aspiration in dentistry). Most of the removed fatty materials are deposited in canister 85 and aerosols are collected in drain bag 79 as mentioned earlier.

Figure 6:
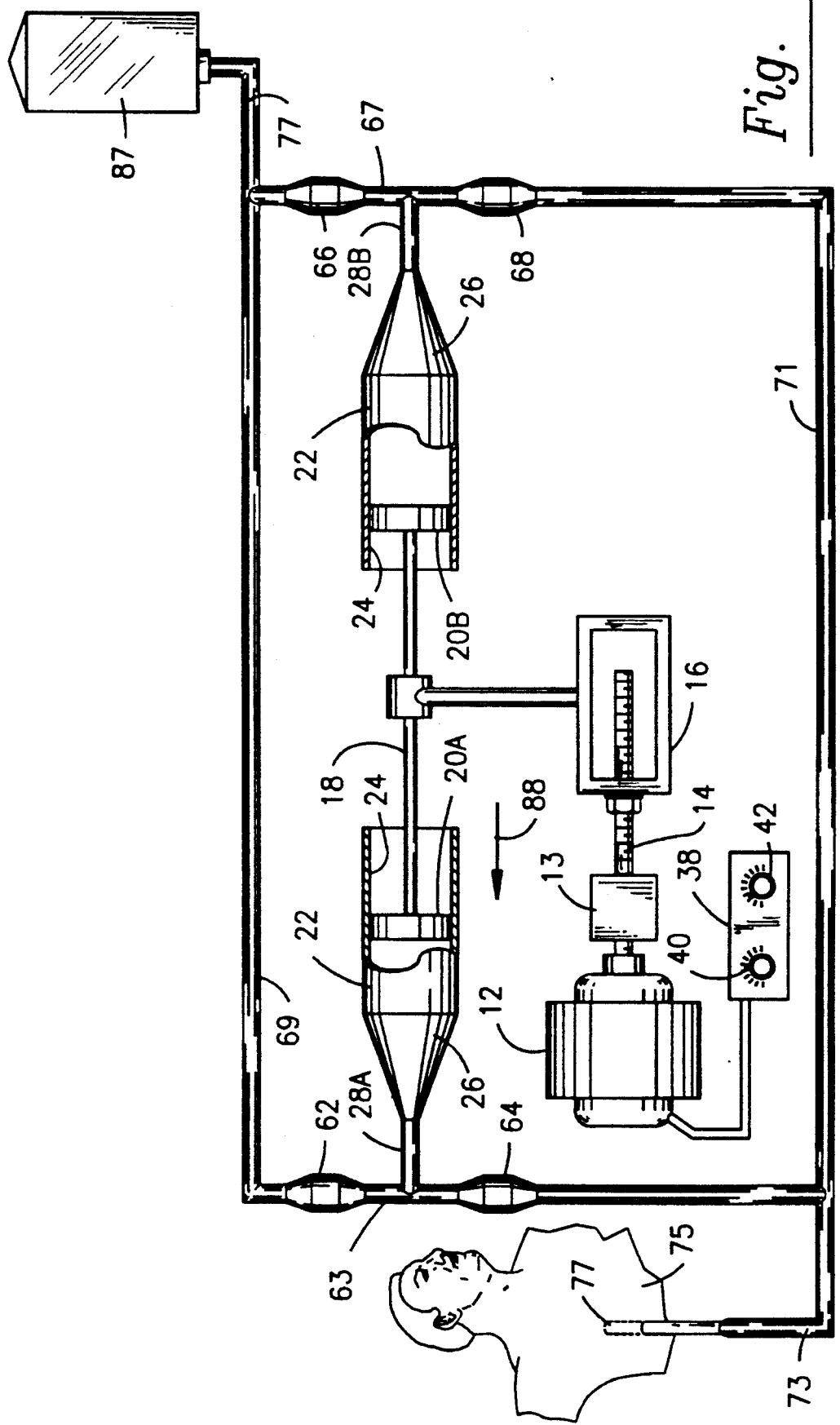
FIG. 6 is a diagrammatic representation of a sixth embodiment of the invention.

As shown in FIG. 6, the same parts will deliver irrigation fluid in bag 87 to the surgical site. The only structural difference between the parts of FIGS. 5 and 6 is the reversal of the position of the check valves 62, 64, 66, and 68 so that the flow is toward the patient and not away therefrom.

The machines of FIGS. 5 and 6 may be used at the same time so that a liposuction or aspiration site is continuously irrigated throughout the liposuction or aspiration process. Thus, two tubular members are introduced into the patient at the surgical site, one of which is connected to the machine of FIG. 5 to provide the vacuum needed for the liposuction or aspiration and the other of which is connected to the machine of FIG. 6 for irrigation purposes. The sharp tip 77 of the liposuction-performing tubular member will cut into the deposits to be removed, and the vacuum will remove the severed material. The tip of the irrigation tube may also be sharpened for the same reason. Thus, there is no need to use a rotating cutting tool as a part of the liposuction procedure; thus, this novel apparatus eliminates the need for such a tool and thus reduced the number of instruments that must be inserted into the patient.

This invention is clearly new and useful. Moreover, it was not obvious to those of ordinary skill in this art at the time it was made, in view of the prior art considered as a whole as required by law.

This invention pioneers the art of dispensing and aspirating systems for high viscosity materials that incorporate small, electrically driven motors in lieu of conventional hydraulic and pneumatic systems. Thus, the claims that follow are to be broadly construed to protect the heart or essence of this breakthrough invention.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. An apparatus for dispensing and aspirating high viscosity materials, comprising:
   a pair of cartridges disposed in axial alignment with one another, each of said cartridges having an open proximal end and a nozzle formed in its distal end;
   each cartridge of said pair of cartridges containing a thixotropic material;
   said cartridges disposed with their respective open proximal ends in facing relation to one another and with their respective nozzles pointing away from one another;
   a pair of movably mounted plungers, each plunger of said pair of plungers being disposed in alignment with an associated cartridge of said pair of cartridges and being reciprocal therewithin;
   means for preventing radial expansion of each cartridge o f said pair of cartridges as said plunger drives high viscosity material through their respective nozzles;
   said means for preventing radial expansion including a nonexpandable metallic sleeve member that ensleeves each cartridge of said pair of cartridges in closely spaced relation thereto;
   a common plunger rod for interconnecting said plunger
   means for imparting a reciprocating linear motion to said plunger rod so that each plunger oscillates within its associated cartridge when said apparatus is operating;
   a drain bag for collecting aerosols of the type produced during a liposuction process;
   a vacuum canister for collecting fatty material of the type produced during a liposuction process;
   a fluid-carrying line means extending from a patient to said vacuum canister, from said vacuum canister to said apparatus, and from said apparatus to said drain bag so that liquid and gaseous fluid flows through said line means when said plungers are reciprocating within their associated cartridges;
   a plurality of one-way valves disposed at predetermined positions in said line means for allowing air flow through said line means in a first direction, said first direction being from said patient toward said vacuum canister and toward said drain bag, said plurality of one-way valves preventing flow of fatty deposits and aerosols into said cartridges, and for blocking air flow through said line in a second direction opposite to said first direction; and
   control means for controlling said apparatus;
   whereby a liposuction procedure is performed by said apparatus.

2. The apparatus of claim 1, wherein said line means has a leading end adapted to slice into fatty deposits so that a liposuction procedure may be performed in the absence of tools other than said apparatus.

3. The apparatus of claim 1, wherein said means for imparting said reciprocating linear motion includes a motor means and translating means associated with said motor means for translating rotary motion to linear motion.

4. The apparatus of claim 1, wherein said control means includes means for independently controlling the number of revolutions of said motor means.

5. The apparatus of claim 1, wherein said means for imparting said reciprocating linear motion is a ball slide and screw assembly.

6. The apparatus of claim 1, wherein said means for imparting said reciprocating linear motion is an acme thread and nut assembly.

7. An apparatus for irrigating a surgical site, comprising:
- a pair of cartridges disposed in axial alignment with one another, each of said cartridges having an open proximal end and a nozzle formed in tis distal end;
- each cartridge of said pair of cartridges containing a thixotropic material;
- said cartridges disposed with their respective open proximal ends in facing relation to one another and with their respective nozzles pointing away from one another;
- means for preventing radial expansion of each cartridge of said pair of cartridges as aid plunger drives high viscosity material through their respective nozzles;
- said means for preventing radial expansion including a nonexpandable metallic sleeve member that ensleeves each cartridge of said pair of cartridges in closely spaced relation thereto;
- a pair of movably mounted plungers, each plunger of said pair of plungers being disposed in alignment with an associated cartridge of said pair of cartridges and being reciprocal therewithin;
- a common plunger rod for interconnecting said plungers;
- means for imparting a reciprocating linear motion to said plunger rod so that each plunger oscillates within its associated cartridge when said apparatus is operating;
- an irrigation bag for holding irrigation fluid of the type having utility in irrigating surgical sites;
- a fluid-carrying line means extending from a patient to said apparatus, and from said apparatus to said irrigation bag so that irrigation fluid flows through said line means when said plungers are reciprocating within their associated cartridges;
- a plurality of one-way valves disposed at predetermined positions in said line means for allowing flow of said irrigation fluid through said line means in a first direction, said first direction being from said irrigation bag toward said patient, said plurality of one-way valves preventing flow of irrigation fluid into said cartridges, and for blocking flow of said irrigation fluid through said line in a second direction opposite to said first direction; and
- control means for controlling said apparatus;
- whereby an irrigation procedure is performed by said apparatus.

8. The apparatus of claim 7, wherein said means for imparting said reciprocating linear motion includes a motor means and translating means associated with said motor means for translating rotary motion to linear motion.

9. The apparatus of claim 7 wherein said control means includes means for independently controlling the number of revolutions of said motor means.

10. The apparatus of claim 7, wherein said means for imparting said reciprocating linear motion is a ball slide and screw assembly.

11. The apparatus of claim 7, wherein said means for imparting said reciprocating linear motion is an acme thread and nut assembly.

* * * * *